United States Patent [19]

Annis et al.

[11] 4,242,583
[45] Dec. 30, 1980

[54] X-RAY IMAGING VARIABLE RESOLUTION

[75] Inventors: Martin Annis, Newton; Edwin Frederick, Concord, both of Mass.

[73] Assignee: American Science and Engineering, Inc., Cambridge, Mass.

[21] Appl. No.: 900,380

[22] Filed: Apr. 26, 1978

Related U.S. Application Data

[63] Continuation of Ser. No. 782,972, Mar. 30, 1977, abandoned.

[51] Int. Cl.² ............................................ G03B 41/16
[52] U.S. Cl. ............................... 250/358 R; 250/360; 250/505
[58] Field of Search ............ 250/505, 416 TV, 358 R, 250/360, 359

[56] References Cited

U.S. PATENT DOCUMENTS

| | | | |
|---|---|---|---|
| 3,866,047 | 2/1975 | Hounsfield | 250/505 |
| 4,031,401 | 6/1977 | Jacob | 250/503 |

*Primary Examiner*—Craig E. Church
*Attorney, Agent, or Firm*—Pollock, Vande Sande & Priddy

[57] ABSTRACT

A scanning X-ray imaging system produces an image of the transmissivity of objects by producing a relative motion of the object generally perpendicular to the triangular planes joining an X-ray point source and M X-ray line detectors, where M is equal to or greater than 1; these X-rays pass through a scanning slit assembly. The scanning slit assembly generally includes a plane of X-ray opaque material having N sets of line slits, where N is equal to or greater than 2, each set containing M identical line slits. The scanning slit assembly, in addition, includes a rotating X-ray opaque material containing N uniquely different sets of radial slits, each set containing identical radial slits. Each of the N sets of radial slits is uniquely paired with each of the N sets of line slits. During any scan of an object, M detectors, M line slits and one of the N sets of radial slits are used. The scanning X-ray imaging system provides N selections in image resolution of the scanned object. The selectivity provides radiographic images with different contrast resolution and/or spatial resolution.

10 Claims, 7 Drawing Figures

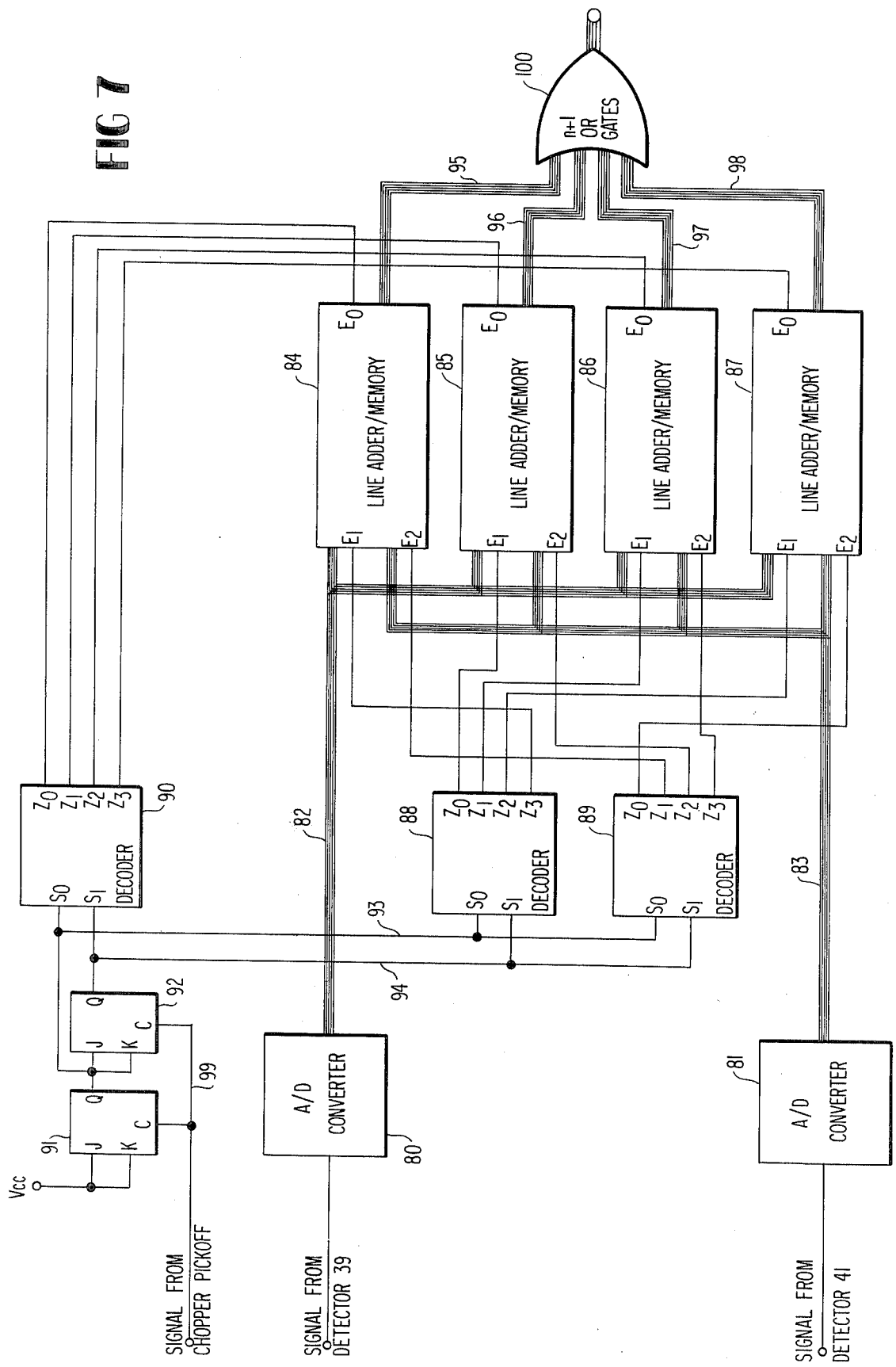

X-RAY IMAGING VARIABLE RESOLUTION

RELATED APPLICATION

This application is a continuation-in-part of our prior co-pending application Ser. No. 782,972, filed Mar. 30, 1977, now abandoned for X-Ray Imaging Variable Resolution.

BACKGROUND OF THE INVENTION

The present invention relates in general to penetrating radiant energy imaging and, more particularly, concerns a novel apparatus and techniques for selectively obtaining X-ray images of variable density contrast and/or spatial resolution with a modification of commercially available MICRO-DOSE ® X-ray apparatus disclosed in U.S. Pat. No. 3,780,291, manufactured and sold by American Science and Engineering, Inc. The invention readily achieves magnification and greater resolution in the image of a scanned object with an improved scanning slit assembly.

The present invention represents an improvement of the invention in U.S. Pat. No. 3,780,291, embodied in the commercially available AS&E ® MICRO-DOSE ® X-ray imaging system used in airports and other locations for parcel inspection. In that system, a moving pencil beam of X-rays repeatedly scans a line detector as the scanned object is translated past the beam and detector assembly. The line detector produces light signals representative of the incident X-ray energy, which are then converted by photoelectric detecting means to video signals representative of the X-ray transmissivity between the beam source and the detector. From the video signals, a video system displays a sequence of horizontal lines to provide a two-dimensional image of the scanned object.

Four radial slits in a rotating disc of X-ray opaque material successively intercept the line beam to produce a pencil beam that scans the length of the line detector as the radial slits rotate; the intersection of one of the four slits and their corresponding line slit moves from one end of the line beam cross-section to the other.

It is an important object of this invention to provide an improved X-ray imagig system.

It is another object of the invention to achieve the preceding object with a system that provides increased density contrast as a trade-off against the size of the area of the object being imaged.

It is still another object of the invention to provide an improved X-ray imaging system that provides increased density contrast without decreasing the area of the object being imaged by increasing the number of detectors.

It is a further object of the invention to achieve one or more of the preceding objects with relatively slight modification of the prior art system described above.

It is still a further object of the invention to achieve one or more of the preceding objects by selectively displacing the relative position between the scanning slit assembly and the detector and X-ray source.

It is still a further object of the invention to achieve one or more of the preceding objects economically and with high reliability while permitting a relatively unskilled operator to easily effect the change in resolution/contrast.

It is still a further object of the invention to utilize essentially the same logic electronics for each of the images constructed using any of the line slit—radial slit combinations.

It is still a further object of the invention to have a fixed spatial relationship between the images formed by each line slit—radial slit combination, allowing a small area of one of the larger images to be easily X-rayed as higher density and/or spatial resolution.

SUMMARY OF THE INVENTION

According to one embodiment of the invention, there is a scanning X-ray imaging system with a line detector and a first X-ray opaque member having at least one slit with lengths aligned essentially along the length of the line detector and a second X-ray opaque member having at least first and second sets of radial slits for relative movement across the line cross-section of the region bounded by the line detector and a said slit in the first member, said first and second sets being radially displaced relative to a common axis of rotation. The first and second members are relatively displaceable in a direction perpendicular to the line cross-section between first and second positions with the first and second sets of slits, respectively, capable of intercepting the line cross-section to provide first and second magnification, spatial resolution, and density contrast, respectively. In a particular form of the invention, there are four outer radial slits and twelve inner radial slits. In the former case, a larger area of the target is scanned four times per revolution and, in the latter, a smaller area is scanned twelve times per revolution. The smaller area receives a greater X-ray dose than the larger area which produces an improved density contrast and/or spatial resolution and image magnification.

Numerous other features, objects and advantages of the invention will become apparent from the following specification when read in connection with the accompanying drawing in which:

BRIEF DESCRIPTION OF THE DRAWING

FIG. 7 is a diagrammatic representation of a data acquisition scheme which will add the signals from each of the two detectors shown in FIGS. 3, 4 and 5 so that the sum of the two detector outputs is spatially coherent.

DETAILED DESCRIPTION OF PREFERRED EMBODIMENTS

Figure 1:
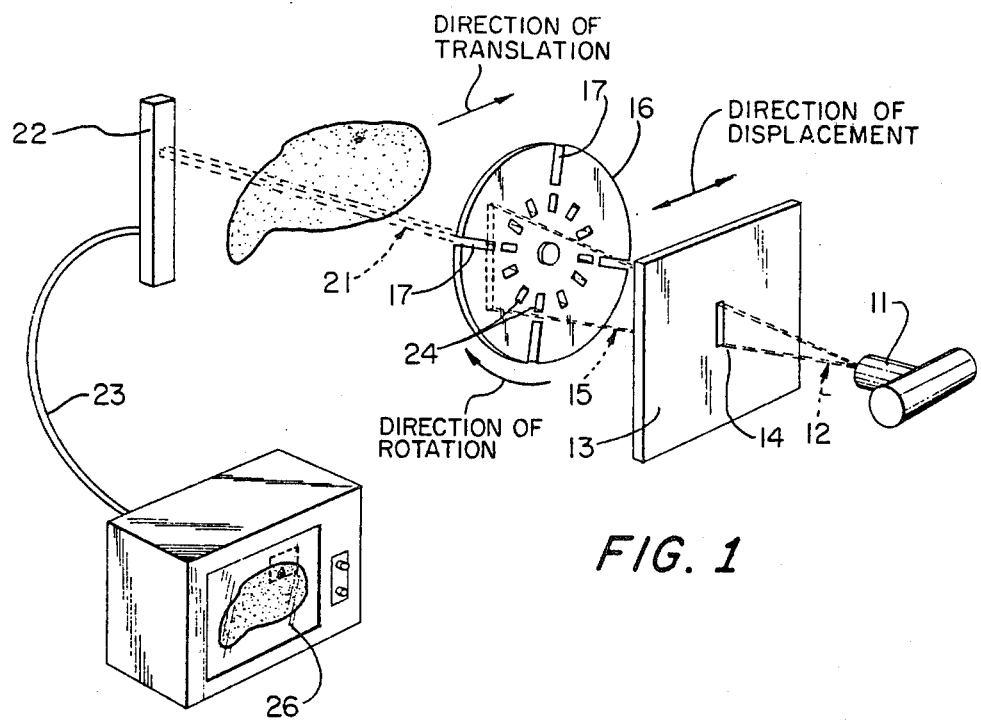
FIGS. 1 and 2 are diagrammatic representations of the scanning slit assembly and detector configurations according to the invention in respective ones of the two positions.

With reference now to the drawing and more particularly FIG. 1 thereof, there is shown a diagrammatic representation of the scanning slit assembly and detector configuration according to the invention. X-ray source 11 emits a cone shaped beam 12, which strikes a first member comprising an X-ray opaque plate 13. Line slit 14 in plate 13 collimates beam 12 into a linear beam 15, which strikes a second member comprising a disc 16. Outer radial slits 17, spaced 90° apart, successively intersect linear beam 15 as disc 16 rotates to produce pencil beam 21 that repeatedly scans the length of a line detector 22 as the intersection of slits 17 and linear beam 15 moves from one end of linear beam 15 to the other. Only one radial slit 17 transmits beam 15 at each instant of time. Detector 22 produces a video signal on output line 23 representative of the X-ray response of the scanned object located in the region between disc 16 and detector 22. As the scanned object is relatively translated to the right, imaging means 26 produces a two dimensional image of the X-ray response of the scanned object in response to the sequence of video signals in a manner known in the art embodied in the commercially available AS&E® MICRODOSE® X-ray inspection system.

Figure 2:
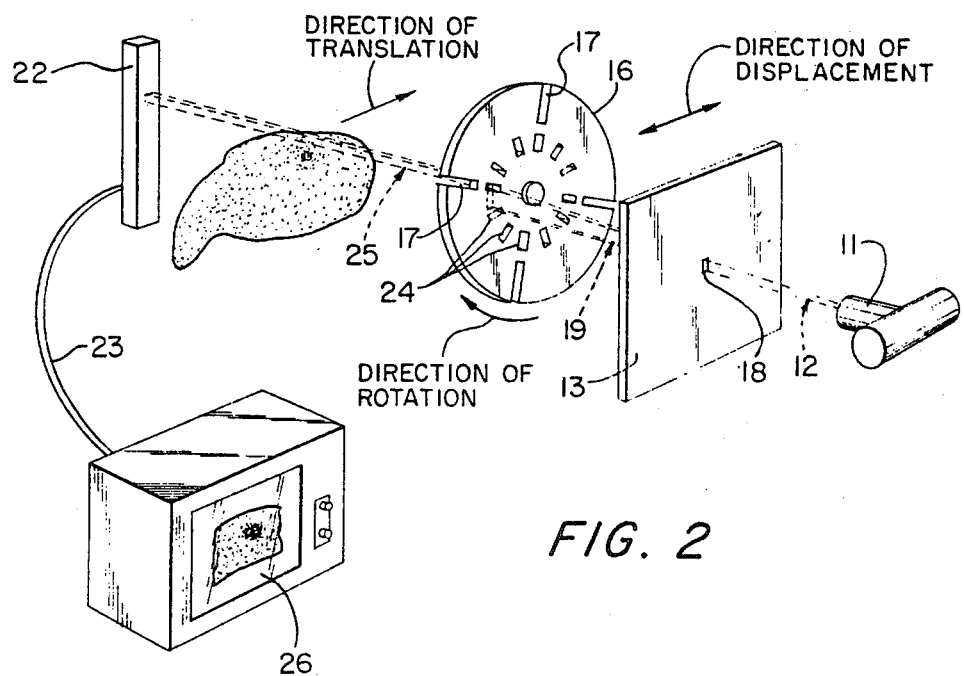

Referring now to FIG. 2, there is shown a diagrammatic representation of the configuration shown in FIG. 1 with disc 16 and plate 13 relatively displaced so that inner radial slits 24 intersect linear beam 19 collimated by slit 18, shorter than slit 14, for facilitating more detailed examination of a smaller area of interest. According to the invention, there are 12 additional radial slits 24 in disc 16, normally set narrower than each slit 17 and at a smaller radius. With disc 16 selectively displaced horizontally in its plane so that radial slits 24 successively intersect linear beam 19, pencil beam 25 of normally smaller cross-section than that of beam 21 repeatedly scans a portion of line detector 22. Only one radial slit transmits X-rays at each instant of time.

Pencil beam 25 scans a smaller portion of the scanned object because the length of line slit 18 is smaller than that of line slit 14. Let $x_1$ be the ratio of the pencil beam 25 area to the smaller scanned area and $x_2$ be the ratio of the pencil beam 21 area to the larger scanned area. It is preferred that $x_1 > x_2$ and the total scanning time for both the smaller scanned area and the larger scanned area is the same. Thus, the smaller area scanned by beam 25 receives $x_1/x_2$ more X-ray dose than the larger area scanned by beam 21. The result is an image with improved resolution and/or contrast, allowing image magnification of the smaller scanned area with increased resolution and contrast to facilitate detailed examination. The line slit 18 and radial slits 24, or line slit 14 and radial slits 17, may be adjustable in width to allow improved spatial resolution at the expense of contrast, or vice versa.

The specific embodiment described is to illustrate the principles of the invention. In a specific embodiment of the invention the chopper disc 16 is 18.8 inches in diameter and includes three sets of slits, each set located at a radius different from the radius of the other sets of slits. These three sets of radial slits and three corresponding line slits are each associated with a particular examination field size. The large field is approximately 15 inches wide by 20 inches long from scanning with four radial slits 17 spaced 90 degrees apart on the outer periphery of disc 16, each of radial length 2.6 inches and adjustable width $\leq 0.03$ inches, each passing over a line slit of length 11.5 inches, adjustable width $\leq 0.08$ inches, and center located 6.0 inches from axis of wheel 16. The medium field is substantially 6 inches by 8 inches by scanning with six radial slits spaced 60 degrees apart each 0.69 inches in radial length and $\leq 0.06$ inches adjustable width, each passing over a line slit of length 4.0 inches, adjustable width $\leq 0.06$ inches, and center located 3.9 inches from the axis of chopper disc 16. The small field is 1.5 inches by 2 inches from scanning with a set of twelve radial slits each of 0.25 inches radial length by $\leq 0.05$ inches adjustable width and spaced 30 degrees apart, each passing over a line slit of length 1.19 inches, adjustable width $\leq 0.05$ inches, and center located 2.8 inches from the axis of the chopper wheel 16. The line and radial slits which form each pair have adjustable width so that contrast may be increased at the expense of spatial resolution or vice versa. The particular means for selectively positioning the chopper disc 16 and the rest of the apparatus and for providing synchronizing signals is not a part of the invention and not described in detail here to avoid obscuring the principles of the invention. There is preferably a separate source of a synchronizing signal for each set of scanning openings in chopper disc 16 so that a synchronizing signal is provided substantially at the beginning of each scan. The specific techniques for providing these synchronizing signals is substantially the same as embodied in the commercially available MICRO-DOSE® X-ray inspection systems of American Science and Engineering, Inc., that uses a single set of slits.

To achieve the translation motion for developing the second dimension of the image, either the object to be scanned may be moved transverse to the beam, or as in the embodiment utilized here, the entire X-ray system comprising source-slit assembly and detector is moved transverse to the object to be scanned.

Although different areas are scanned depending upon which set of slits generate the X-ray pencil beam, the television display area is the same so that using the small field provides to the observer a display of the smaller area of interest magnified ten times over that of the large field display.

The specific means for storing and displaying the video signals derived from the individual scans is also not a part of the invention and may comprise analog storage, such as a silicon storage tube, video disc and film with readout by a conventional television display having 1023 lines and capable of storing 60 levels of gray scale. Alternatively, digital storage may be used that may comprise a Data General NOVA 3 computer using a magnetic disc system and a video image processor with magnetic tape and film functioning for permanent record and television readout displaying 480×640 picture elements and capable of storing a gray scale of $2^{12}$ levels.

While the exemplary embodiment disclosed herein includes a rotating disc formed with sets of like apertures with the sets radially displaced and means for selectively displacing the chopper disc 16 in a direction transverse to the plane of linear beam 15 or linear beam 19, it is within the principles of the invention to use other scanning techniques. For example, the scanner might comprise a chopper of a geometrical form other than a disc. An alternate to the disc chopper is the drum chopper generally of the type disclosed in the Belgian Pat. No. 839519 granted Mar. 31, 1976, in which the rim contains the radial slits. An advantage of the drum chopper is that it may scan an object that has to remain against some physical boundary, such as the floor. Another advantage of the drum chopper is that the angle between each radial slit in the rim is always 90° with respect to the line slit. This feature is advantageous when used with a multiple detector scanner because more than one pencil beam can be generated in such a manner that the spatial alignment of the intersections of each pencil beam with its dedicated line detector remains fixed during each complete scan of the detectors, and the pencil beams are of substantially constant rectangular crosssection during each scan. This fixed alignment allows a much more simplified summation technique for adding the intensities of each pencil beam that is transmitted through each point on the scanned object; for the disc chopper in FIG. 1, the angle between each radial slit 17 and the line slit 14 varies from 45° through 90° to 135°; for the disc chopper in FIG. 2, the angle between each radial slit 24 and line slit 18 varies from 75° through 90° to 105°. The purpose of using the multiple detector scanner shown in FIGS. 3 and 4, instead of the single detector scanner as shown in FIGS. 1 and 2 is to increase density contrast.

Figure 3:
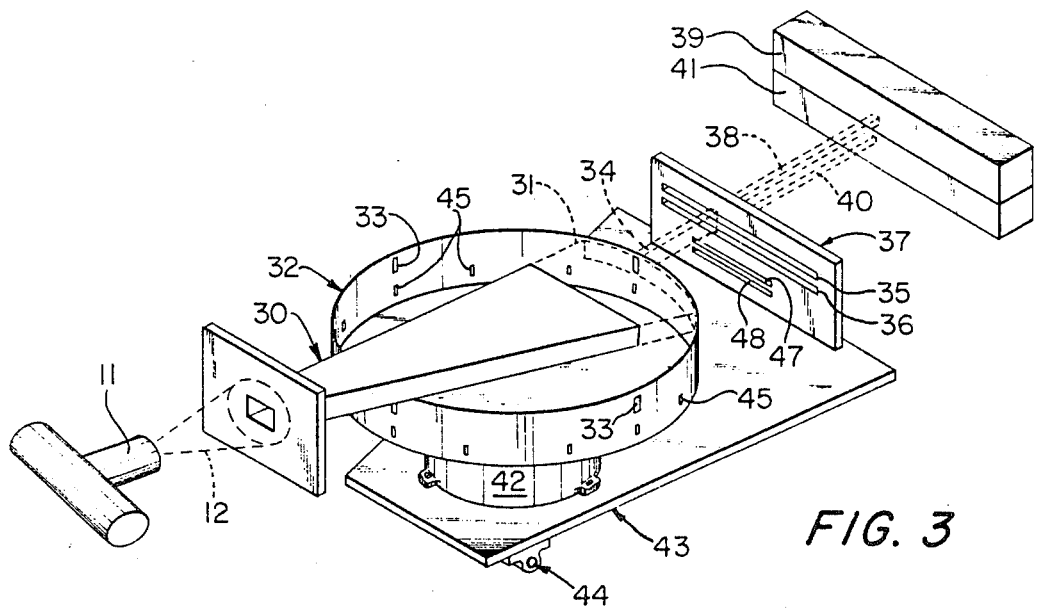
FIGS. 3 and 4 are diagrammatic representations of a scanning slit assembly and detector configuration according to the invention in respective ones of two positions in which multiple pencil beams simultaneously scan multiple detectors according to the invention.

With reference now to FIG. 3, there is shown a diagrammatic representation of the variable resolution drum chopper scanning slit assembly and multiple detector configuration according to the invention. X-ray source 11 emits a coneshaped beam 12, part of which enters triangular-shaped X-ray collimator 30. The reactangular cross-section of collimator 30 collimates beam 12 into a rectangular beam 31, which strikes the inside rim of rotating drum 32. The rim of X-ray opaque material contains the radial slits. Upper radial slits 33, spaced 90° apart, successively intersect rectangular beam 31 as drum chopper 32 rotates to produce slit beam 34 that repeatedly scans the length of line slits 35 and 36 located on X-ray opaque plate 37. Only one radial slit transmits X-rays at each instant of time. Line slit 35 collimates the upper part of slit beam 34 to produce pencil beam 33 that repeatedly scans the length of line detector 39; line slit 36 collimates the lower part of slit beam 34 to produce pencil beam 40 that repeatedly scans the length of line detector 41. The crosssections of pencil beams 38 and 40 are made equal to each other.

To easily convert the scanner in the large field mode as shown in FIG. 3 to the small field mode, the motor 42 for the drum chopper 32 and the X-ray opaque plate 37 are mounted on the supporting structure 43, which can rotate through a small angle about axis 44, which is perpendicular to the concentric axes of drum 32 and motor 42. As a result of the small rotation about axis 44, upper radial slits 33 pass above rectangular beam 31 and line slits 35 and 36 are above the plane containing the X-ray collimator 30 and rectangular beam 31.

Figure 4:
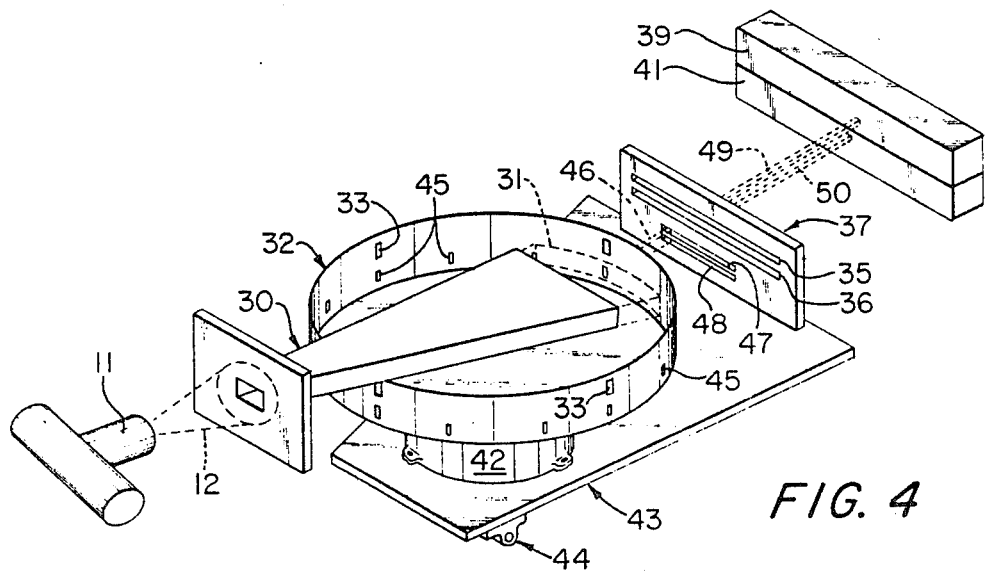

Referring now to FIG. 4, there is shown a diagrammatic representation of the configuration shown in FIG. 3, but with drum 32 and plate 37 relatively rotated so that lower radial slits 45 intersect with rectangular beam 31 for facilitating more detailed examination in a small field mode. According to the invention, there can be 12 additional radius slits 45 in drum chopper 32, normally set narrower than each slit 33. With drum 32 selectively rotated so that radial slits 45 successively intersect rectangular beam 31 as drum 32 rotates to produce slit beam 46, slit beam 46 of normally narrower cross-section than that of slit beam 34 repeatedly scans the length of line slits 47 and 48 located on plate 37. Line slit 47 collimates the upper part of slit beam 46 to produce pencil beam 49 that repeatedly scans the length of line detector 39; line slit 48 collimates the lower part of slit beam 46 to produce pencil beam 50 that repeatedly scans the length of line detector 41. Pencil beams 49 and 50 have equal cross-sections and are normally set smaller than the cross-sections of pencil beams 38 and 40. Only one pencil beam is generated for each detector at any instant of time.

If the object to be scanned moves down past line detectors 39 and 41, or the scanning system moves up past a stationary object to be scanned so that there is relative motion between the object and the scanner, the output signal provided by detector 39 is preferably digitized and stored in a linear array memory. When the second line detector 41, which provides an output signal that is digitized at the same rate as for detector 39, corresponds to the same object's spatial transmissivity as represented by the data stored in a particular memory array, the spatially related digitized intensities are added together, converted to an analog video signal, and then transmitted over a video cable to an imaging means which produces a two-dimensional image of the X-ray response of the scanned object in a manner known in the art embodied in commercially available AS&E ® MICRO-DOSE ® X-Ray Inspection System. If a computer system is used for storing and displaying the images, the digitized intensities are preferably not converted back into an analog signal until the moment the representative summed intensities are displayed by the imaging means.

The goal is to insure that the signals from detectors 39 and 41 which are summed correspond to the same portion of the object being scanned, i.e., spatially coherent. Since the detectors 39 and 41 are spaced from one another, the signals that they detect simultaneously in time are not those signals which should be added together, rather, depending on the direction of relative movement between the object and the detectors, one or the other of the detectors will detect spatial transmissivity of a given portion of the object at one time, and at a later time, the other detector will respond to the spatial transmissivity of the same portion of the object being scanned. Thus, the goal is achieved by providing the proper delay between the outputs of detectors 39 and 41 so that the spatial transmissivity signals corresponding to the identical portion of the object. While it is appreciated that a wide variety of apparatus can be assembled in accordance with the preceding disclosure to perform this function, one example of such apparatus will be described below.

FIG. 7 illustrates the apparatus referred to. As shown in FIG. 7, the ouput of detector 39 is provided to an A/D converter 80 and the output of detector 41 is provided to an A/D converter 81. The outputs cf the A/D converters 80 and 81 are coupled in parallel to a plurality of linear array memories 84–87, each capable of storing data representing a complete sweep, and further, having a characteristic that a set of signals corresponding to a single sweep when coupled to any of the linear array memories 84–87 will be summed with the previously stored signal retained therein, if any. As shown in FIG. 7, cables 82 and 83 couple the converters 80, 81 to the linear array memories, where each cable may include a separate conductor for each output bit of the A/D converter. This, it will be appreciated, is not necessary to the invention and the several bit outputs of the A/D converter could be coupled in a timed multiplex fashion, if desired. For the illustrated example, each linear array memory includes a pair of inputs corresponding to the output of A/D converter 80, and corresponding to the output of A/D converter 81. To selectively enable the inputs, a pair of decoders 88 and 89 are provided, each with a number of outputs corresponding to the number of linear array memories, with different outputs coupled respectively to enabling inputs $E_1$ or $E_2$ of the different array memories. Each of the decoders 88 and 89 has an $S_0$ and $S_1$ select input thereto. One of these inputs is coupled to a Q output of a JK flip-flop 92 and the other of these inputs is coupled to a Q output of a JK flip-flop 91. The Q output of flip-flop 91 is coupled to the J and K inputs of the flip-flop 92 and the J and K inputs of flip-flop 91 are coupled to a suitable potential. In order to identify the beginning of each sweep, the drum 32 provides a suitable output signal. This output signal can be provided by any one of a number of means known in the art. For example, an X-ray detector can be positioned just outside of the drum 32 at a location where any sweep would start, and the output of this detector is the chopper pickoff signal referred to in FIG. 7. On the other hand, those skilled in the art will perceive that conventional optical, magnetic or electromechanical techniques can also be employed to produce the chopper pickoff signal. In any event, the chopper pickoff signal, identifying the beginning of any sweep, is coupled over the line 99 to clock the flip-flops 91 and 92. The Q outputs of the flip-flops 91 and 92 are coupled to $S_0$ and $S_1$ inputs, respectively, of a third decoder 90, which also has four outputs coupled respectively to enable the different ones of the linear array memories to read out its contents. The outputs of the various linear array memories are coupled over cables to an OR gate network 100 or the equivalent. The output of the OR gate network 100 thus produces the summed signals as desired.

The apparatus of FIG. 7 operates as follows. During any selected sweep, data from detector 41 are digitized and stored in a memory we will refer to as memory 1; prior to this sweep, memory 1 has been cleared, as will become clear hereinafter. Simultaneously, during the scan, data from detector 39 are digitized and added to the data residing in the memory we will term S+1. During this particular sweep of the pencil beams (at any arbitrary time during the sweep) the data stored in a further one of the linear array memories, which we will term S+2, are transferred to a conventional two-dimensional digital image memory in the same manner as would be done directly if only one detector were used. After these data are transferred, this memory S+2 is cleared. The only requirement being that the data must be transferred out of memory S+2 and the memory must be cleared before the sweep is completed. At the beginning of the next sweep of the pencil beams, the memory we have previously denominated as S+2 becomes memory 1, and all other memory numbers are incremented. As we will now show, this arrangement results in digital data from two detectors being added in a spatially coherent manner.

Assume that the relative movement required between the X-ray scanning apparatus and the object being scanned results in relative movement of the scanning apparatus downwardly of the object being scanned at a constant speed (the speed v) perpendicular to the plane of the X-rays. We further assume that the time interval t required for the pencil beam 38 to be spatially located where pencil beam 40 is located at the beginning of the interval is twice the time interval between two successive sweep starts of the pencil beams.

The intensities of the X-ray pencil beams 38 and 40, when incident on the detectors 39 and 41, respectivly, are each converted into representative voltage signals and then digitized by the associated A/D converters 80 and 81. Since the detector 41 physically leads detector 39 in motion (in this example) then the data from this detector must be delayed by two sweep starts. This is accomplished by utilizing the four linear array memories 84–87. The input selection of these four memories are controlled by the decoders 88 and 89 and the effective output of the linear array memories is selected by decoder 90. These dedocers are, in turn, controlled by a 4-bit binary circulating counter comprising the flip-flops 91 and 92.

Utilizing Boolean algebra notation for the switching logic, if $S_0=0$ on conductor 93 (the output of flip-flop 91) and $S_1=0$ on conductor 94 (the output of flip-flop 92) after the beginning of the first sweep start, then $Z_0=1$ and $Z_1=Z_2=Z_3=0$, at the output of the decoders 88–90. Accordingly, in this configuration, the output of the linear array memory 84 is read out through the OR gate 100. The linear array memories 85–87 are disabled from outputting by the decoder 90. On the other hand, decoder 88 enables linear array memory 85 to respond to a signal from detector 39 and decoder 89 allows the linear array memory 87 to respond to the output of dector 41. At the conclusion of reading out of memory 84, the memory is cleared. When the next sweep start is encountered, the flip-flops 91 and 92 are clocked, $S_0=1$ and $S_1=0$; accordingly, the decoder output $Z_0=Z_2=Z_3=0$ and $Z_1=1$. Under these circumstances, the output of memory 85 is read out and following the read out operation, is cleared. The output of detector 39 is input to the linear array memory 86 and the output of detector 41 is input to the linear array memory 84 (this memory having been cleared just prior to the beginning of this sweep). At the initiation of the third sweep, the flip-flops are again clocked so that $S_0=0$ and $S_1=1$. The corresponding decoder outputs are $Z_0=Z_1=Z_3=0$ and $Z_2=1$. Under these circumstances, the linear array memory 86 is read out and then cleared and the data from detector 39 is coupled to linear array memory 87 whereas the output of detector 41 are coupled to a linear array memory 85. On the next sweep, the output of detector 39 is coupled to linear array memory 84, the output of detector 41 is coupled to memory 86 and memory 87 is read out and cleared. Following this sweep, the cycle then repeats. Table I below illustrates this operation for two complete cycles, that is, eight sweeps. The left hand column identifies the sweep number, i.e., starting with sweep 1 and ending at sweep 8, and there is a column for each of the linear array memories 84–87.

TABLE I

| Sweeps | Line Adder/Memories | | | |
|---|---|---|---|---|
| | 84 | 85 | 86 | 87 |
| 1 | ROC | 39 | — | 41 |
| 2 | 41 | ROC | 39 | — |
| 3 | — | 41 | ROC | 39 |
| 4 | 39 | — | 41 | ROC |
| 5 | ROC | 39 | — | 41 |
| 6 | 41 | ROC | 39 | — |
| 7 | — | 41 | ROC | 39 |
| 8 | 39 | — | 41 | ROC |

For any sweep the reference characters 39 or 41 indicate that the memory receives data from the corresponding detector whereas the shorthand ROC refers to the fact that during this sweep the linear array memory is read out and cleared. Reference to the Table shows that after the first sweep, memories 85 and 87 contain data from detectors 39 and 41, respectively, and memory 84 is read out and cleared. Assuming sweep 1 was the first sweep, there would have been no data in the memory. The second sweep results in the readout of memory 85 which contains only data from detector 39. On the third sweep, memory 86 is read out and cleared, it, too, only contains data from the detector 39. On sweep 4, however, when linear array memory 87 is read out, it contains data from both detectors 39 and 41 which are summed therein. Since the input to memory 87 from detector 39 is displaced two sweeps from the input from detector 41, and since it takes exactly two sweeps as we have assumed for a selected portion of the object to travel from one detector to the other, the signals summed and read out of memory 87 during the fourth sweep are spatially coherent. Further review of Table I will show that on succeeding sweeps linear array memories 84, 85, 86 and again 87 are read out and cleared at which time each has contained spatially coherent sum of signals from the detectors 39 and 41.

If we assume that the A/D converters 80 and 81 produce N bit words, summation of a pair of these may require as many as N+1 bits and therefore the output of the memories contains a number of conductors equal to one more than the input. These N+1 bits of data are coupled to a conventional two-dimensional image storage digital memory via N+1 separate four input OR gates (one input for each of the memories). All N+1 OR gates are symbolically represented by the OR gate 100.

The data read out on output conductors 95-98 represents a single line of the objects' transmissivity. Because the single line of data was created by two X-ray scans instead of one, the radiographic contrast is improved. Assuming a noiseless detector and noiseless electronic circuits preceding the digitization of the data by the A/D converters 80 and 81, the signal-to-noise ratio of the digitized transmissivity would be increased by a factor of $\sqrt{2}$. This enhanced readout signal can then be coupled to an imaging means to produce a two-dimensional image as already explained.

The X-ray line detectors used in the multiple detector scanner are each similar to the single X-ray line detector 22 shown in FIGS. 1 and 2. However, in a dual detector system, it is preferred to construct each scintillator crystal of each of the detectors 39 and 41 in FIGS. 3 and 4 with a square cross-section. The square cross-sections permit the pair of pencil beams 38 and 40, or pencil beams 49 and 50, to be as close as possible; the closer the pair of pencil beams are to each other, the fewer linear array memories required for a given scan speed and given translation motion speed.

Figure 5:
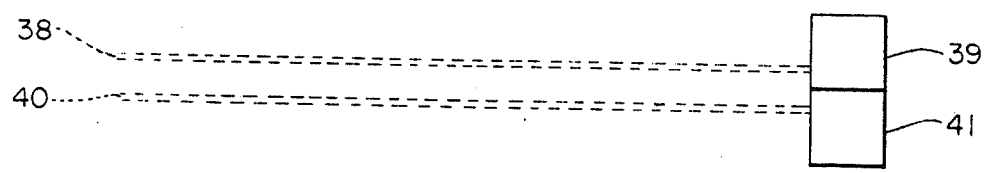
FIG. 5 is a diagrammatic representation of the crossection of the side-by-side detectors shown in FIGS. 3 and 4.

Referring now to FIG. 5, there is shown a diagrammatic representation of the cross-section of the detectors 39 and 41. In a specific embodiment of the invention, the scintillator crystal for each detector is NaI(Tl) with a cross-section of 1.5 inches by 1.5 inches and 32 inches long. The total separation between the two crystals is 1/16 inch, and they are optically isolated. This configuration allows the two pencil beams 38 and 40 to be closer to each other at the detectors than the two crystals' center-to-center distance of 1 9/16 inches; the actual pencil beam separation used in the specific embodiment is approximately ¾ inch; crystals made at the dimensions of ½ inch ×½ inch ×32 inches are preferably not used because of the large light attenuation for such a small cross-section over the length of 32 inches. The ratio of the square root of cross-section area to length is thus greater than 1/64 and preferably of the order of 3/64.

Figure 6:
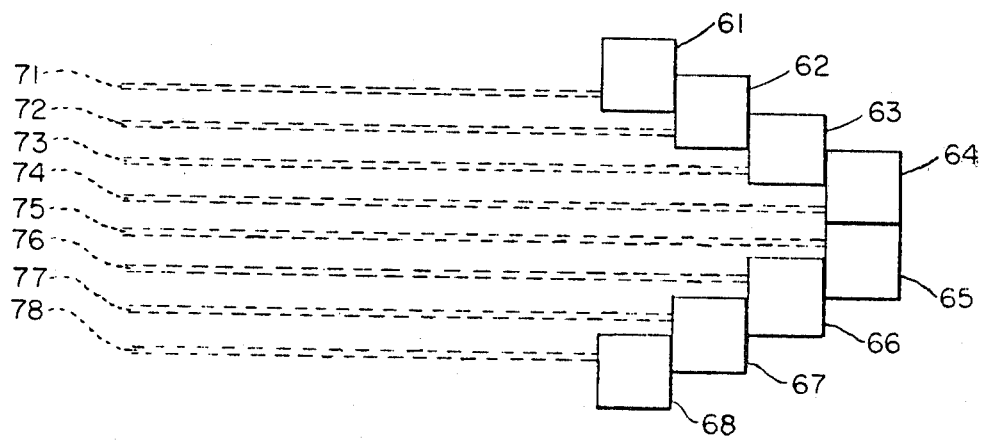
FIG. 6 is a diagrammatic representation of the crossection of a multiple detector system using more than two detectors in a stepped configuration.

Referring now to FIG. 6, there is shown a diagrammatic representation of the cross-section of a multiple detector system using more than two detectors. In this staircase configuration, the long crystal detectors 61, 62, 63, 64, 65, 66, 67 and 68, each of a particular dimension, such as 1.5 inches by 1.5 inches by 32 inches long, may be arranged in the manner shown such that the multiple series of X-ray pencil beams 71, 72, 73, 74, 75, 76, 77 and 78 may scan the entire 32 inch lengths of the multiple detector with equal spacings, as close as is feasible, and the detector outputs for corresponding points of the object being scanned cumulatively combined to further enhance density contrast. It is also clear that any number of detectors may be used in this arrangement to further enhance density contrast.

The specific means for adding intensities is not a part of this invention and many techniques may be practiced by those skilled in the art. Thus, computer memories may store digitized representations of the density signal for an object provided by each detector, and the computer may add the representations for each point to provide a sum signal for each point that may be visually displayed. While digital techniques are preferred, analog techniques may be used. For example, video output signals from the different detectors may be applied to respective video storage tubes which may then be scanned to provide a number of stored video signals that are added together to provide a combined video signal with enhanced density contrast.

There has been described a novel X-ray imaging system characterized by selectively variable resolution, contrast and magnification, simple operation by relatively unskilled operators and numerous other features. It is evident that those skilled in the art may now make numerous uses and modifications of and departures from the specific embodiments described herein without departing from the inventive concepts. For example, the disclosure herein has been in terms of pencil beams scanning straight lines at the interception of the pencil beam and a plane-in-space representing the displayed image. However, the line slit or slits could also be curved, if desired, so the intersection of the pencil beam or beams with the plane-in-space comprises curves. The only restriction is that for the case of multiple pencil beams, all curves must be parallel on the representative plane-in-space. Consequently, the invention is to be construed as embracing each and every novel feature and novel combination of features present in or possessed by the apparatus and techniques herein disclosed and limited solely by the spirit and scope of the appended claims.

What is claimed is:

1. Radiant energy imaging apparatus for imaging an object as said object is traversed relative to said imaging apparatus comprising:
   sources of at least first and second pencil beams of penetrating radiant energy,
   at least first and second radiant energy detecting means in fixed relationship to said sources and extending perpendicular to a path of relative motion described by said object, for providing at least first and second detected output signals respectively representative of the intensity of said radiant energy upon said first and second detecting means,
   means for scanning with said first and second pencil beams along said first and second radiant energy detecting means respectively to provide first and second image signals respectively representative of the radiant energy response of the object in a region traversed by said first and second pencil beams along first and second paths respectively to said first and second detecting means, and means for cumulatively combining said first and second image signals so that the portions of the signals combined represent the radiant energy response of corresponding portions of the object in said region to provide a combined image signal having enhanced contrast density relative to that of either of said first and second image signals.

2. Radiant energy imaging apparatus in accordance with claim 1 wherein said penetrating radiant energy comprises X-rays.

3. Radiant energy imaging apparatus in accordance with claim 1 wherein said source of at least first and second pencil beams of radiant energy comprises, a source of said radiant energy, means for collimating said radiant energy into a fan-like beam, and means defining at least first and second relatively fixed apertures for intercepting said fan-like beam to provide said first and second pencil beams respectively, said means for scanning comprising means for relatively moving said first and second apertures and said fan-like beam to effect said scanning.

4. Radiant energy imaging apparatus in accordance with claim 3 wherein said means defining said at least first and second relatively fixed apertures comprises first and second slits that are transparent to said penetrating radiant energy in a substantially cylindrical rim that is opaque to said penetrating radiant energy, and said means for relatively moving comprising means for rotating said rim to move said at least first and second slits along said fan-like beam.

5. Radiant energy imaging apparatus in accordance with claim 3 wherein said at least first and second slits are substantially perpendicular to the plane of said fan-like beam to produce said first and second pencil beams of substantially constant rectangular cross-section that remain in fixed relationship during scanning.

6. Radiant energy imaging apparatus in accordance with claim 1 wherein, said first and second detecting means comprises first and second contiguous scintillating crystals for converting incident penetrating radiant energy into light energy, and first and second photodetecting means responsive to the light energy provided by said first and second scintillating crystals respectively for providing said first and second image signals respectively each amplitude modulated in proportion to the instantaneous penetrating radiant energy flux incident upon said first and second scintillation crystals respectively.

7. Radient energy imaging apparatus in accordance with claim 1 wherein said first and second radiant energy detecting means defines first and second adjacent substantially parallel lines.

8. A method of radiant energy imaging of a medium which method includes the steps of, scanning with at least first and second pencil beams of penetrating radiant energy at least first and second radiant energy detecting means respectively to provide at least first and second image signals respectively representative of the penetrating radiant energy response of the medium in a region transversed by said first and second pencil beams along paths terminating on said first and second detecting means, relatively displacing an object in said region and an assembly comprising the source of said first and second pencil beams and said first and second detecting means to establish relative translating motion in a direction transverse to each plane in which said first and second pencil beams scan to produce first and second sequences of image signals respectively representative of the radiant energy response of said object in two dimensions, and cumulatively combining said first and second sequences of image signals so that the portions of said first sequence combined with the portions of said second sequence are representative of the penetrating radiant energy response of a corresponding portion of said object to produce a combined sequence of image signals characterized by contrast density that is greater than that of either of said first and second sequences of image signals.

9. The apparatus of claim 1 wherein:

said means for cumulatively combining comprises accumulating means for summing said first and second image signals.

10. The method of claim 8 in which said step of cumulatively combining comprises the step of adding.

* * * * *